(12) United States Patent
Böttcher et al.

(10) Patent No.: US 6,521,767 B1
(45) Date of Patent: Feb. 18, 2003

(54) METHOD FOR SUSPENSION HYDROGENATION OF AN ANTHRAQUINONE COMPOUND IN A SPECIAL REACTOR IN ORDER TO PRODUCE HYDROGEN PEROXIDE

(75) Inventors: Arnd Böttcher, Frankenthal (DE); Jochem Henkelmann, Mannheim (DE); Franz Josef Bröcker, Ludwigshafen (DE); Gerd Kaibel, Lampertheim (DE); Heinz Rütter, Hochdorf-Assenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,852

(22) PCT Filed: Mar. 1, 1999

(86) PCT No.: PCT/EP99/01324

§ 371 (c)(1),
(2), (4) Date: Aug. 28, 2000

(87) PCT Pub. No.: WO99/43611

PCT Pub. Date: Sep. 2, 1999

(30) Foreign Application Priority Data

Feb. 27, 1998 (DE) .......................................... 198 08 385

(51) Int. Cl.⁷ .............................. C07J 53/00; C01B 7/07
(52) U.S. Cl. ........................ 552/500; 552/501; 423/587
(58) Field of Search .................................. 552/501, 500; 423/587

(56) References Cited

U.S. PATENT DOCUMENTS 4,428,923 A * 1/1984 Kunkel et al. ............... 423/588
5,939,589 A * 8/1999 Kaibel et al. ................ 568/568

FOREIGN PATENT DOCUMENTS

| DE | 938 252 | 1/1956 |
|---|---|---|
| DE | 196 11 976 | 10/1997 |
| EP | 0 672 617 | 9/1995 |
| GB | 718307 | 11/1954 |

OTHER PUBLICATIONS

Ullmans Encyclopedia of Industrial Chemistry, vol. A13, pp. 447–456, "Hydrogen Peroxide," 5th Edition.

* cited by examiner

*Primary Examiner*—Alton Pryor
(74) *Attorney, Agent, or Firm*—Oblon, Spivak, McClelland, Maier & Neustadt, P.C.

(57) ABSTRACT

In a process for the suspension hydrogenation of an anthraquinone compound or a mixture of two or more thereof in a reactor in which there are present the working solution in which at least one catalyst is suspended and, in addition, a hydrogen-containing gas phase, the working solution and the gas phase are, in the reactor, passed at least partly through a fitting having openings or channels whose hydraulic diameter is from 0.5 to 20 mm, preferably from 1 to 10 mm, particularly preferably from 1 to 3 mm.

20 Claims, 3 Drawing Sheets

METHOD FOR SUSPENSION HYDROGENATION OF AN ANTHRAQUINONE COMPOUND IN A SPECIAL REACTOR IN ORDER TO PRODUCE HYDROGEN PEROXIDE

This application is a 371 of PCT/EP99/01324 filed Mar. 1, 1999.

The present invention relates to a process for the suspension hydrogenation of anthraquinone compounds in a special reactor for preparing hydrogen peroxide by the anthraquinone process. In the hydrogenation process of the present invention, an anthraquinone compound or a mixture of two or more thereof are brought into contact with a suspension catalyst and a hydrogen-containing gas phase in a special reactor as is comprehensively described in DE-A 196 11 976. This special reactor contains fittings having openings or channels which have a particular hydraulic diameter.

Virtually all the hydrogen peroxide produced worldwide (>2 million metric tons/a) is produced by the anthraquinone process.

The process is based on the catalytic hydrogenation of an anthraquinone compound to form the corresponding anthrahydroquinone compound followed by reaction of the latter with oxygen to form hydrogen peroxide and subsequent isolation of the hydrogen peroxide formed by extraction. The catalysis cycle is closed by renewed hydrogenation of the anthraquinone compound which has been formed again in the oxidation step.

An overview of the principal reactions is given in the scheme below:

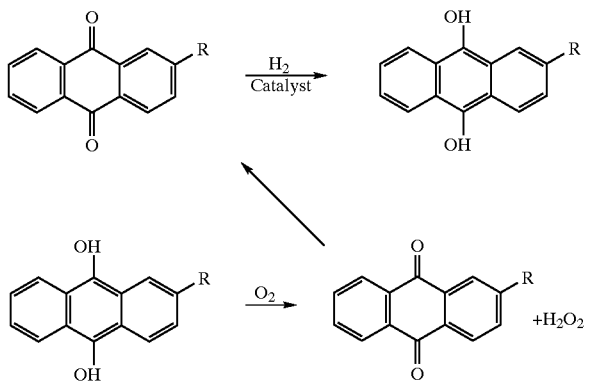

In this reaction, the anthraquinone compounds are generally dissolved in a mixture of a plurality of organic solvents. The resulting solution is referred to as the working solution. In the anthraquinone process, this working solution is generally passed continuously through the above-described steps of the process.

An overview of the anthraquinone process is given in Ullmanns Encyclopedia of Industrial Chemistry, 5th Edition, Vol. A13, pp. 447–456.

A particularly important step in the anthraquinone process is the hydrogenation step in which the anthraquinone compound present in the working solution is hydrogenated in the presence of a catalyst to form the corresponding anthrahydroquinone compound.

The present invention relates to this hydrogenation step of the anthraquinone process.

This catalytic hydrogenation can be carried out in suspension or in a fixed bed in various types of reactor. The prior art is detailed, for example, in EP 0 672 617.

In a fixed-bed process, the hydrogen-containing gas phase and the working solution are passed in cocurrent or countercurrent through a reactor which is charged with a supported catalyst coated with noble metal. The catalyst used loses activity over time and therefore has to be regenerated or replaced. For this purpose, the fixed-bed catalyst first has to be removed from the reactor and fresh or regenerated catalyst has to be installed. This is very time-consuming and expensive.

In industry, the hydrogenation step is therefore primarily carried out in the suspension mode since a drop in the activity of the catalyst can be countered by continuous introduction and bleeding-off of the catalyst.

In its most general form, the suspension hydrogenation is carried out in a reactor in which there are present the working solution in which at least one catalyst is suspended and, in addition, a hydrogen-containing gas phase.

The technology of suspension reactors in general is comprehensively described in Ullmanns Enzyklopädie der technischen Chemie, 4th Edition, Volume 3, pp. 494–518.

Some reactors which are used for the suspension hydrogenation of anthraquinone compounds are described in Ullmanns Enzyklopädie der technischen Chemie, 4th Edition, Volume 17, pp. 700–702. These include stirred vessels, bubble columns and moving bed reactors.

As catalysts for the suspension hydrogenation of anthraquinone compounds, use is made of either suspension catalysts or supported suspension catalysts. The latter comprise a metal layer on a support particle. Supported suspension catalysts have the advantage that the particle diameters of from 0.06 to 0.15 mm simplify the recirculation of the catalyst to the reactor compared to unsupported suspension catalysts. In addition, they are generally, in terms of their activity, less sensitive to thermal stresses and poisoning than are pure catalysts.

The suspension hydrogenation of an anthraquinone compound using a loop reactor containing palladium black as catalyst is described in U.S. Pat. No. 4 428 923.

In DE-C 938 252, the hydrogenation of the anthraquinone compound is carried out in a bubble column containing tubular internal fittings in which the introduction of hydrogen into the lower part of each tube leads to upward flow of the working solution in the tubes. The catalyst used is a supported, palladium suspension catalyst (e.g. 2% of Pd on activated aluminum oxide).

The basic problem in suspension reactions is to ensure sufficient contact of the reactants with the catalyst particles which are suspended in the liquid phase.

Suspension reactors require the introduction of mechanical energy, which is, for example, introduced by means of stirrers, nozzles or rising gas bubbles, to suspend the solid particles. Increasing this mechanical energy input above that required for suspension leads, however, to no appreciable improvement in the mass transfer between the liquid and the suspended solid particles since the achievable relative velocity exceeds the sedimentation velocity only insignificantly.

A decisive factor for economical operation of an anthraquinone process is a high space-time yield in the hydrogenation step.

The space-time yield is the amount of product formed per unit catalyst volume and per unit time.

Using the reactors which have hitherto been used according to the prior art for the suspension hydrogenation of anthraquinone compounds for preparing hydrogen peroxide it has not always been possible to achieve sufficiently high space-time yields.

It is an object of the present invention to provide a process for the suspension hydrogenation of an anthraquinone compound using a reactor which has hitherto not yet been used for this hydrogenation.

We have found that this object is achieved by the process described in the claims. In this process for carrying out the suspension hydrogenation of an anthraquinone compound or a mixture of two or more thereof in a reactor in which there is present the working solution in which at least one catalyst is suspended and, in addition, a hydrogen-containing gas phase, the working solution and the gas phase are, in the reactor, passed at least partly, i.e. part of their volume for part of their path, through a fitting having openings or channels whose hydraulic diameter is from 0.5 to 20 mm, preferably from 1 to 10 mm, particularly preferably from 1 to 3 mm. The hydraulic diameter is defined as the ratio of 4 times the cross section of the opening and its circumference.

The choice of the channel width which is ideal in an individual case depends primarily on the viscosity of the liquid passed through, the size of the suspended particles and the type of gas phase. The more viscous the liquid, the greater the channel widths have to be. For liquids having dynamic viscosities of from $10 \times 10^{-5}$ to $200 \times 10^{-5}$ standard $s/m^2$, hydraulic diameters in the range from 1 to 4.5 mm are optimal.

In this way, higher space-time yields are obtained than in conventional reactors for the suspension hydrogenation of anthraquinone compounds.

For the purposes of the present process, the hydrogenation step is generally carried out at from about 20 to 120° C., preferably from about 30 to 80° C. The pressures employed are generally from about 1 to 20 bar, preferably from about 2 to 10 bar.

The hydrogenation can be carried out using either pure hydrogen or a hydrogen-containing gas.

The hydrogenation is generally carried out to a conversion of from about 50 to 70% in order to achieve a higher selectivity of, in general, >90%, preferably >95%.

The term "anthraquinone compound" includes, in principle, all anthraquinone compounds and the corresponding tetrahydroanthraquinone compounds which can be used for the anthraquinone process for preparing hydrogen peroxide. Anthraquinone compounds which are preferably used for the process of the present invention are 2-alkylanthraquionone such as 2-ethyl-, 2-tert-butyl-, 2-amyl-, 2-methyl-, 2-butyl-, 2-isopropyl-, 2-sec-butyl- or 2-sec-amylanthraquinone and polyalkylanthraquinones such as 1,3-diethylanthraquinone, 2,3-dimethylanthraquinone, 1,4-dimethylanthraquinone or 2,7-dimethylanthraquinone, and also the corresponding tetrahydroanthraquinone compounds, as well as mixtures of two or more thereof.

Solvents which can be used are all the solvents known from the prior art for anthraquinone or anthrahydroquinone compounds. Preference is given to mixtures of two or more solvent components since such solvent mixtures are best able to take account of the different solubility properties of anthraquinone and anthrahydroquinone compounds. Examples which may be mentioned are mixtures of methylnaphthalene and nonyl alcohol, methylnaphthalene and tetrabutylurea, polyalkylated benzene and alkyl phosphates or methylnaphthalene, tetrabutylurea and alkyl phosphates.

As catalysts, it is possible to use all catalyst systems known from the prior art and suitable for a suspension process, e.g. Raney nickel or Pd black. A distinction is made between unsupported catalyst and supported catalysts. Catalysts used are metals, preferably noble metals. Unsupported catalysts which can be used for the purposes of the process of the present invention are all metals of transition group VIII of the Periodic Table. Preference is given to using platinum, rhodium, palladium, cobalt, nickel or ruthenium or a mixture of two or more thereof; particular preference is given to using ruthenium as catalyst. Among the metals of transition groups I and VII of the Periodic Table which can likewise be used as unsupported catalysts and can likewise all be used in principle, preference is given to using copper and/or rhenium. Furthermore, it is possible to use metal salts or oxides such as rhenium sulfides, copper chromides, zinc chromides, nickel oxides, molybdenum oxides, aluminum oxides, rhenium oxides and zinc oxides as catalysts for the purposes of the process of the present invention.

Preference is given to using supported suspension catalysts. These consist of support particles which are coated with metals, preferably noble metals. Active metals which can be used for such catalysts are, in principle, all metals of transition group VIII of the Periodic Table. As active metals, preference is given to using platinum, rhodium, palladium, cobalt, nickel or ruthenium or a mixture of two or more thereof; particular preference is given to using ruthenium as active metal. Among the metals of transition groups I and VII of the Periodic Table which can likewise all be used in principle, preference is given to using copper and/or rhenium.

Although it is possible in principle to use all support materials known for catalyst production, preference is given to using activated carbon, silicon carbide, aluminum oxide, silicon oxide, silicon dioxide, titanium dioxide, zirconium dioxide, magnesium oxide, zinc oxide, calcium carbonate, barium sulfate or mixtures thereof, more preferably aluminum oxide and zirconium dioxide.

The active metal content of the supported suspension catalysts used is generally from about 0.01 to about 30% by weight, preferably from about 0.01 to about 5% by weight and in particular from about 0.1 to 5% by weight, in each case based on the total weight of the catalyst used.

In the process of the present invention, the catalyst particles have an increased relative motion opposite the liquid phase because they experience braking relative to the surrounding working solution in the narrow openings and channels. This braking can be caused both by collisions with the channel walls and by brief retention of the particles on rough wall surfaces.

In the process of the present invention, it is possible to use suspended catalyst particles having a mean particle size of from 0.0001 to 2 mm, particularly preferably from 0.001 to 0.1 mm, more preferably from 0.005 to 0.05 mm. With their high surface area per unit volume, these particles give good results because they are in relative motion opposite the working solution as a result of passing through the narrow internal fittings. As a result, significantly higher space-time yields can be achieved. It has been found experimentally that even a low relative motion of the catalyst particles or a braking of only a small part of the catalyst particles leads to acceleration of the reaction.

The fitting having openings or channels within the reactor for conducting the starting material phase can be in the form of a bed, a knitted article, an open-celled foam, preferably of plastic (e.g. polyurethane or melamine resin) or ceramics, or a packing element as is already known in principle, i.e. in terms of its geometric form, from distillation or extraction technology. Such packing elements, which offer the advantage of a low pressure drop, are, for example, wire mesh packings of the types Montz A3 and Sulzer BX, DX and EX. However, for carrying out the process of the present invention, the packings have a hydraulic diameter which is significantly, usually by a factor of from 2 to 10, smaller than that of comparable internal fittings in the field of distillation or extraction technology. Wire mesh packings are particularly advantageous. This is presumably because part of the suspension does not follow the channels formed but penetrates through the mesh. However, for the purposes of the process of the present invention, it is also possible to use packings made of other woven, knitted or felted, liquid-permeable materials in place of mesh packings. Further suitable packings used are flat metal sheets, preferably without perforations or other large openings, for example corresponding to the types Montz B 1 or Sulzer Mellapak. Expanded metal packings, for example, packings of the type Montz BSH, are also advantageous. In these too, openings such as perforations have to be kept appropriately small. The decisive aspect for suitability of a packing for the purposes of the present invention is not its geometry, but the sizes of openings or widths of channels available for flow in the packing.

In the process of the present invention, the working solution and the gas phase are preferably passed through openings or channels whose wall materials have surface roughnesses in the range from 0.1 to 10 times, preferably from 0.5 to 5 times, the mean particle size of the suspended catalyst particles. The roughening of the openings or channel walls effects particularly good braking and thus relative motion of the suspended catalyst particles. These are presumably held briefly on the wall surfaces so that they experience a delay before returning to the liquid stream. The preferred roughness of the material used depends in the individual case on the size of the suspended catalyst particles.

Furthermore, in the process of the present invention, the working solution and the hydrogen-containing gas phase are preferably passed through openings or channels having metallic wall materials whose surfaces have a mean roughness $R_a$ in accordance with DIN 4768/1 of from 0.001 to 0.01 mm. Such metal surfaces can be produced, for example, by thermal treatment of steels, for example Kanthal (Material No.: 1.4767), in an oxygen atmosphere. Thus, it is not only macroscopic but microscopic roughnesses which are effective for the purposes of the present invention.

The process of the present invention is preferably carried out by passing the liquid phase through the fitting having openings and channels at an empty tube velocity of from about 50 to 300 $m^3/m^2h$, preferably from 150 to 200 $m^3/m^2h$. The empty tube velocity of the gas phase is preferably from 0.15 to 8.5 cm/s, particularly preferably from 2.5 to 5.5 cm/s.

The process of the present invention can be carried out continuously or batchwise.

The reactor in which, according to the present invention, the hydrogenation of the anthraquinone compounds takes place can be any reactor type known from the prior art for suspension reactions, e.g. jet nozzle reactors, bubble columns, moving-bed reactors, tube reactors, multitube reactors and stirred vessels. In the case of a stirred vessel, the above-described internal fittings can also be fixed directly to the stirrer shaft and can take over at least part of the function of a stirrer. They can also additionally act as baffles. The above-described internal fittings preferably but not necessarily fill the entire reactor, except when employed in stirred vessels. The reactor is preferably an upright bubble column through which the reactants preferably flow in cocurrent from the bottom upward. Another preferred reactor type is a heatable or coolable multitube reactor in which the internal fittings are accommodated in the individual tubes. The reactants preferably flow through this reactor in cocurrent from the bottom upward. Another suitable type of reactor is a stirred vessel in which the internal fittings are integrated into the baffles and/or stirrers.

The reactor has facilities for introducing and taking off the working solution and the gas phase.

The suspended catalyst material can be introduced and separated off again by means of customary techniques (sedimentation, centrifugation, flat bed filtration, crossflow filtration.

The suspended solids are separated out by the customary separation methods, for example flat bed filtration or candle filtration. In the case of a continuous reaction, crossflow filtration has been found to be particularly useful.

BRIEF DESCRIPTION OF DRAWINGS

The present invention is described in detail with the aid of the following figures. In the figures:

FIG. 1 shows, by way of example, an experimental arrangement incorporating a discontinuously operated bubble column reactor 1 in which, as specified by the present invention, there is arranged a mesh packing 2 whose geometry is comparable to the distillation packing Sulzer BX. To carry out the reaction, the working solution containing suspended catalyst is first introduced via the filling line 3. The hydrogen-containing gas phase is fed in via the connection line 4 and is mixed in a mixing nozzle 5 with suspension being pumped around the circuit and this mixture is introduced into the reactor 1 at its lower end. The suspension together with gas is discharged from the reactor via line 6 and is passed to the separation vessel 7. From there the gas is passed through a waste gas cooler 8 and via a pressure maintenance device 9 into the waste gas line 10. The suspension goes from the separation vessel 7 via line 11 to the pump 12, the heat exchanger 13, the mixing nozzle 5 and further to the reactor 1. After the reaction is complete, the suspension is drained via the take-off line 14. FIG. 2 shows a continuously operated bubble column 1 provided with packings 2, which column is additionally supplied via lines 15 and 16 with circulating gas which, together with a hydrogen-containing fresh gas 4, is mixed by means of the mixing nozzle 5 into the suspension 11 which is being circulated. The output from the reactor is passed via line 6 to the separation vessel 7 in which the gas phase is separated off and discharged via line 15. To limit the accumulation of gaseous impurities, a substream of this gas is taken off via line 10 and the remaining gas is returned to the reactor via line 16. Only liquid working solution is introduced via line 3. The suspended catalyst remains in the reactor system as a result of it being held back by means of a crossflow filter 17 and only catalyst-free liquid 14 leaving and being taken off.

FIG. 3 shows the embodiment which is preferably employed in the case of fast reactions with a high heat of reaction; in this embodiment, the reactor 1 has the configuration of a shell-and-tube heat exchanger and comprises tube bundles 18 in which wire mesh packings 2 are arranged. The heat exchanger 8 shown in FIGS. 1 and 2 can be omitted in this embodiment. It can be retained to take on the function of a preheater at the beginning of is the reaction if the reactor is to be supplied only with coolant. The functions of the parts 4, 5, 6, 7, 10, 12, 14, 16 and 17 correspond to those in FIG. 2.

Figure 1:
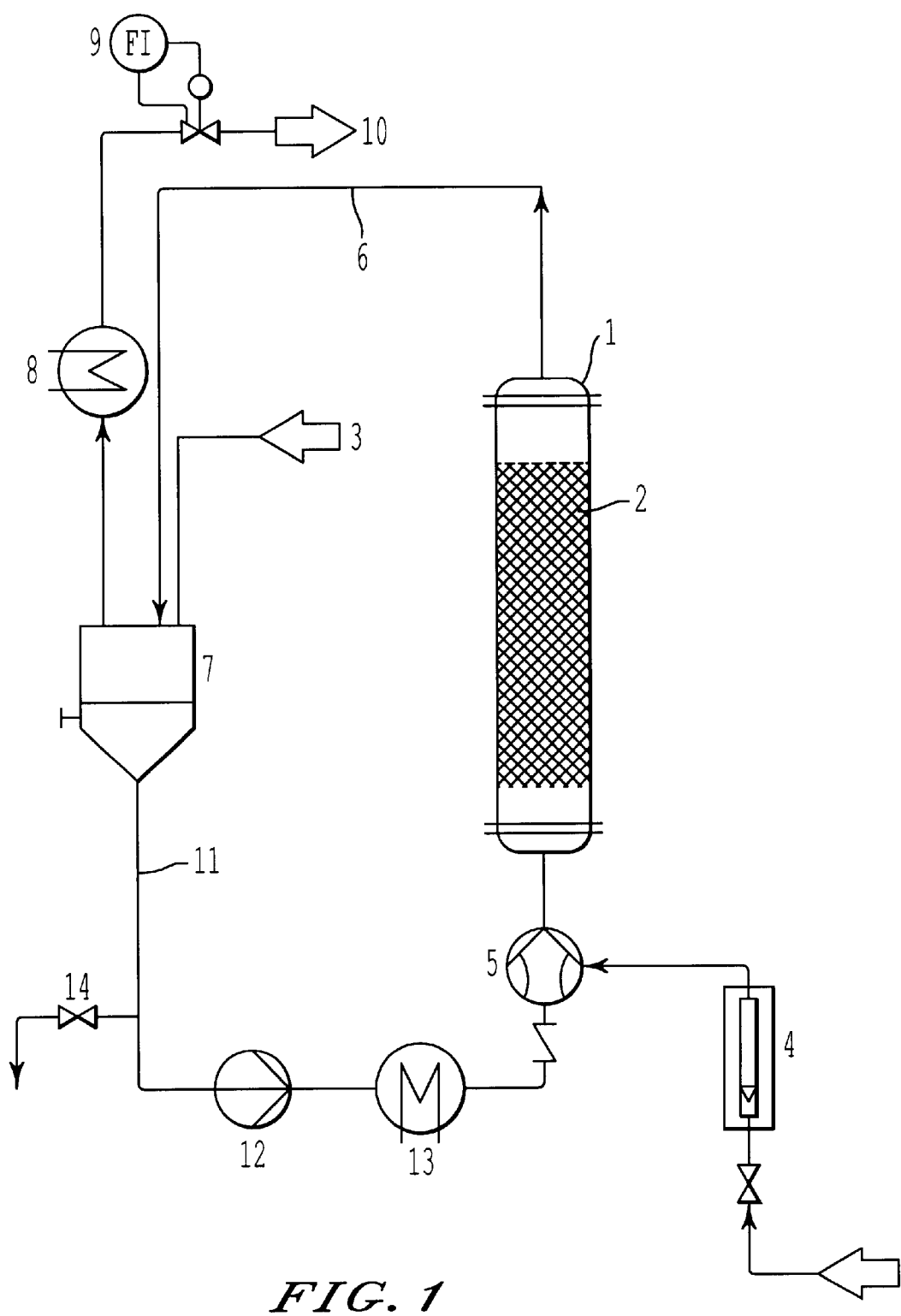
FIG. 1: Experimental arrangement for batchwise hydrogenation of an anthraquinone compound in a special bubble column
Figure 2:
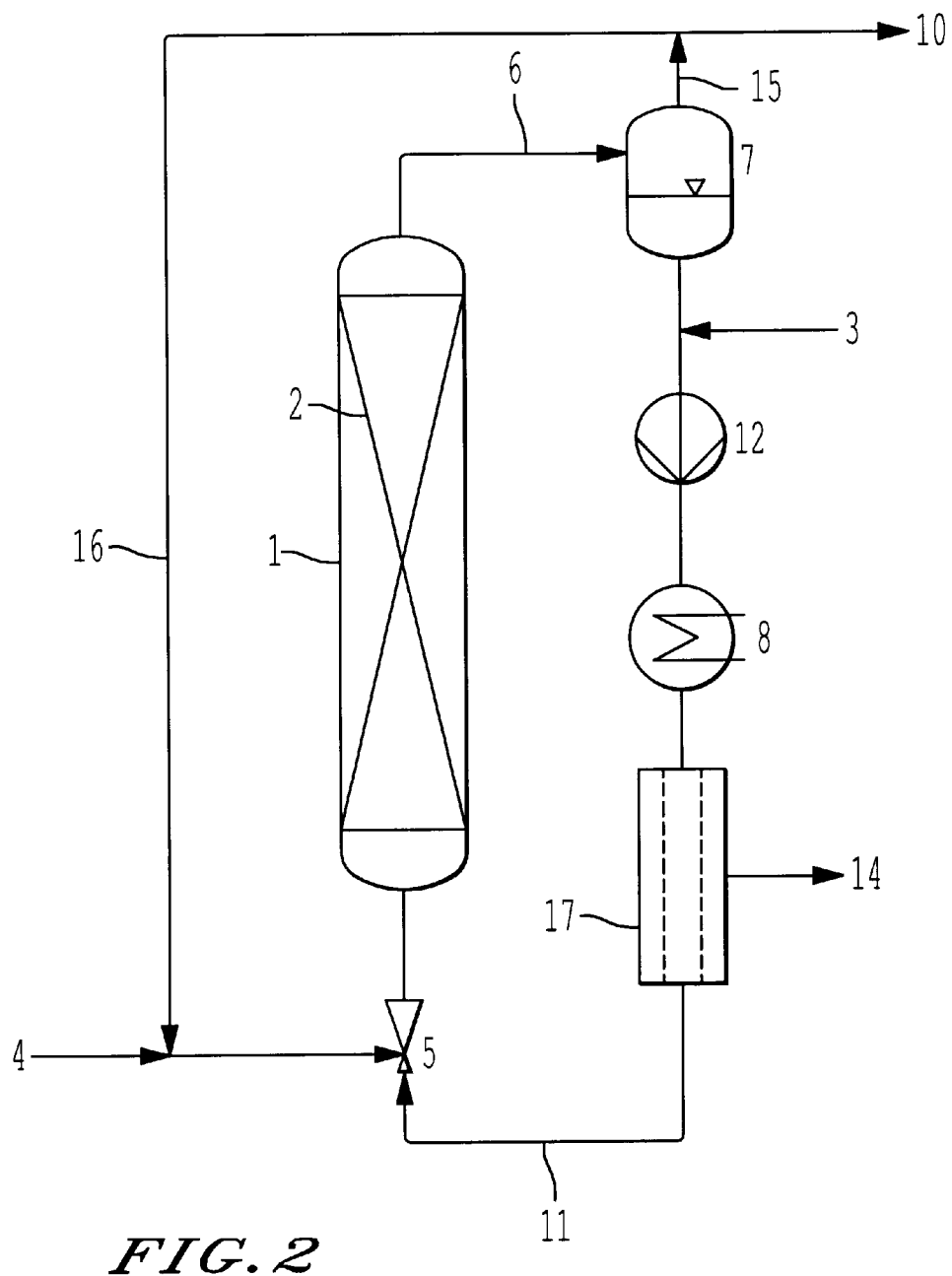
FIG. 2: Experimental arrangement for continuous hydrogenation of an anthraquinone compound in a special bubble column
Figure 3:
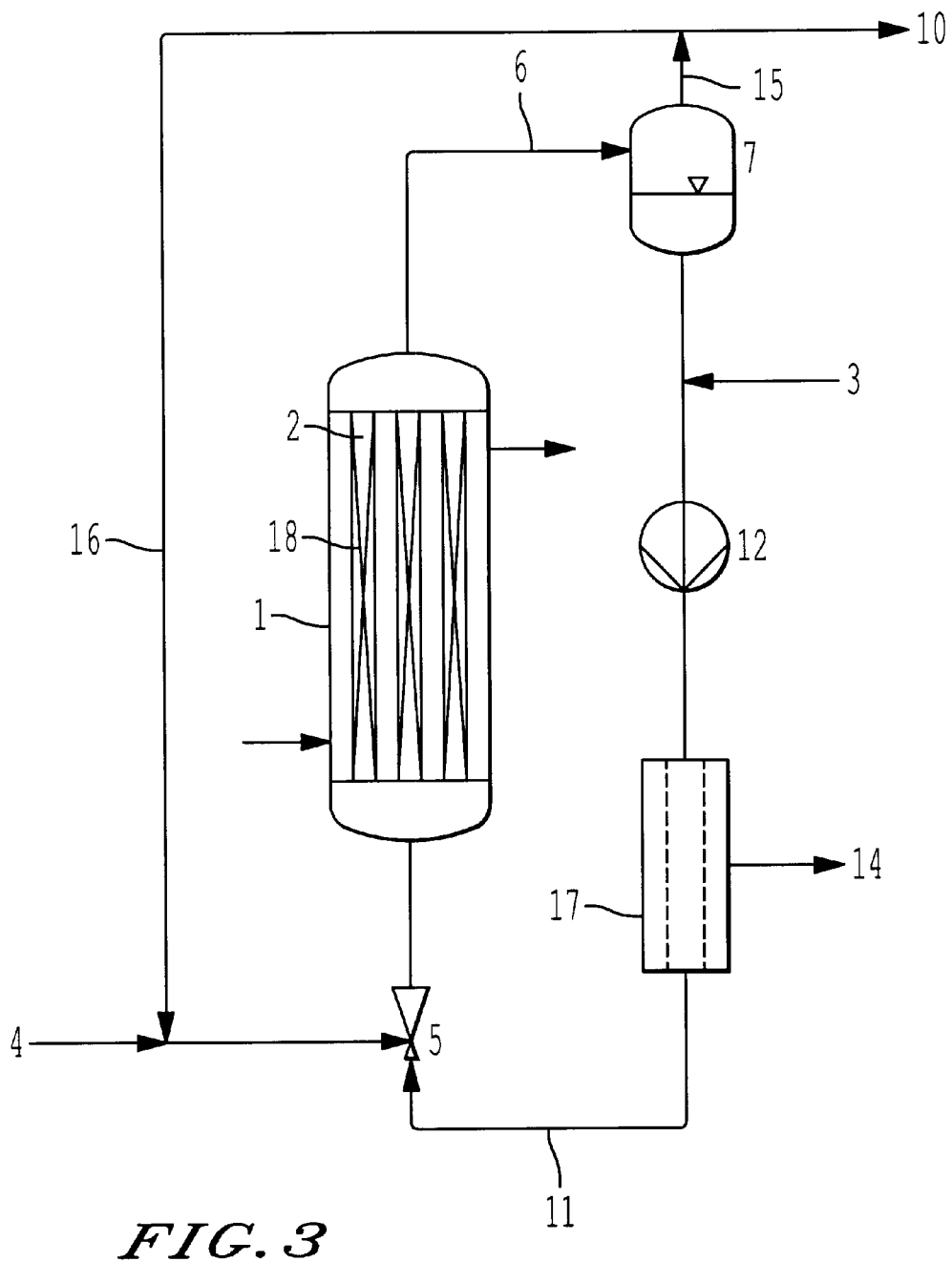
FIG. 3: Experimental arrangement for continuous hydrogenation of an anthraquinone compound in a special multi-tube reactor

The further details described in DE-A 196 11 976 with regard to the reactor, the process procedure, the experimental arrangement, the catalyst used and the packing elements used apply analogously in the context of the process of the present invention.

The present invention is illustrated by the example below:

EXAMPLE

The batchwise hydrogenation of 2-ethylanthraquinone (13% strength solution in Shellsol/tetrabutylurea (70:30)) was carried out at 30° C. and ambient pressure both in a conventional 1 l stirred vessel fitted with a three-bladed sparging stirrer (1000 rpm) and also in a bubble column (400 mm high, 40 mm in diameter) provided with mesh packing. As suspension catalyst, use was made of 1.5 g of Pd on aluminum oxide (Pd content: 5%). The amount of working solution used was in both cases 650 ml.

a) Stirred vessel: hydrogenation was carried out for a total of 3 hours. After 3 hours, 50% of the 2-ethylanthraquinone used had been converted into 2-ethylanthrahydroquinone (determined by means of gas chromatography).

b) Packed bubble column: hydrogenation was carried out for a total of 3 hours. After 3 hours, 65% of the 2-ethylanthraquinone used had been converted into 2-ethylanthrahydroquinone (determined by gas chromatography).

We claim:

1. A process for hydrogenating an anthraquinone compound or a mixture thereof, said process comprising passing in a reactor a working solution containing at least one suspended catalyst and at least one anthraquinone compound together with a hydrogen-containing gas phase at least partly through an internal fitting arranged within the reactor and having a plurality of openings or a plurality of channels, at least one of the plurality of openings and plurality of channels having a hydraulic diameter of 0.5 to 20 mm.

2. A process as claimed in claim 1, wherein the at least one suspended catalyst comprises suspended catalyst particles having a mean particle size of 0.0001 to 2 mm.

3. A process as claimed in claim 1, wherein the internal fitting comprises at least one of a bed, a knitted article, an open-celled foam and a packing element.

4. A process as claim 1, wherein the working solution and the hydrogen-containing gas phase are at least partly passed through openings or channels whose wall materials have surface roughnesses in the range from 0.1 to 10 times the mean particle size of the suspended catalyst particles.

5. A process as claimed in claim 1, wherein the working solution and the hydrogen-containing gas phase are passed through openings or channels having metallic wall materials whose surfaces have a mean roughness $R_a$ in accordance with DIN 4768/1 of from 0.001 to 0.01 mm.

6. A process as claimed in claim 1, wherein the working solution is passed through the internal fitting at an empty tube velocity of 50 to 300 $m^3/m^2h$.

7. A process as claimed in claim 1, wherein the reactor comprises an upright bubble column.

8. A process as claimed in claim 1, wherein the reactor is a heatable or coolable multitube reactor, where the internal fitting is installed in individual tubes.

9. A process as claimed in claim 1, wherein the reactor is a stirred vessel and the internal fitting is integrated into at least one of baffles and stirrers.

10. A process as claimed in claim 1, wherein the at least one suspended catalyst comprises a supported suspension catalyst.

11. A process as claimed in claim 10, wherein the supported suspension catalyst is coated with a metal selected from the group consisting of metals in transition group VIII of the Periodic Table.

12. A process as claimed in claim 1, wherein the working solution is passed through the internal fitting at an empty tube velocity of 150 to 200 $m^3/m^2h$.

13. A suspension hydrogenation process for hydrogenating an anthraquinone compound, comprising the steps of:

preparing a working solution containing at least one suspended catalyst and at least one anthraquinone compound; and passing the working solution together with a hydrogen-containing gas phase at least partly through a reactor including an internal fitting having at least one of a plurality of openings and a plurality of channels with a hydraulic diameter of 0.5 to 20 mm.

14. A suspension hydrogenation process as claimed in claim 13, wherein the at least one suspended catalyst comprises suspended catalyst particles having a mean particle size of 0.0001 to 2 mm.

15. A suspension hydrogenation process as claimed in claim 13, wherein the working solution is passed through the internal fitting at an empty tube velocity of 50 to 300 $m^3/m^2h$.

16. A suspension hydrogenation process as claimed in claim 13, the at least one suspended catalyst comprises a supported suspension catalyst.

17. A suspension hydrogenation process as claimed in claim 16, wherein the supported suspension catalyst is coated with a metal selected from the group consisting of metals in transition group VIII.

18. A suspension hydrogenation process as claimed in claim 13, wherein the at least one anthraquinone compound comprises at least one of 2-alkylanthraquinone selected from the group consisting of 2-ethyl-anthraquinone, 2-tert-butyl-anthraquinone, 2-amyl-anthraquinone, 2-methyl-anthraquinone, 2-butyl-anthraquinone, 2-isopropyl-anthraquinone, 2-sec-butyl-anthraquinone, and 2-sec-amy-anthraquinone, polyalkylanthraquinone selected from the group consisting of 1,3-diethylanthraquinone, 2,3-dimethylanthraquinone, 1,4-dimethylanthraquinone, and 2,7-dimethylanthraquinone, and corresponding tetrahydroanthraquinone thereof.

19. A suspension hydrogenation process as claimed in claim 13, wherein the working solution comprises a solvent mixture selected from the group consisting of a mixture of methylnaphthalene and nonyl alcohol, a mixture of methylnaphthalene and tetrabutylurea, a mixture of polyalkylated benzene and alkyl phosphates or methylnaphthalene, and a mixture of tetrabutylurea and alkyl phosphates.

20. A suspension hydrogenation process as claimed in claim 13, wherein the at least one anthraquinone compound is derived from oxidation of at lease one anthrahydroquinone compound for production of hydrogen peroxide.

* * * * *

UNITED STATES PATENT AND TRADEMARK OFFICE
CERTIFICATE OF CORRECTION

PATENT NO.     : 6,521,767 B1
DATED          : February 18, 2003
INVENTOR(S)    : Boettcher et al.

It is certified that error appears in the above-identified patent and that said Letters Patent is hereby corrected as shown below:

Title page, Item [54] and Column 1, lines 1-5,
Title should read -- [54] SUSPENSION HYDROGENATION OF AN ANTHRAQUINONE COMPOUND IN A SPECIAL REACTOR FOR PREPARING HYDROGEN PEROXIDE --

Signed and Sealed this

Fifteenth Day of July, 2003

JAMES E. ROGAN
*Director of the United States Patent and Trademark Office*